(12) United States Patent
Delka et al.

(10) Patent No.: US 10,376,427 B2
(45) Date of Patent: Aug. 13, 2019

(54) UNDERGARMENT SYSTEM WITH ABSORBENT FLAP

(71) Applicant: ACT Holding, LLC, Olathe, KS (US)

(72) Inventors: Ryan K. Delka, Fort Collins, CO (US); Bret Delka, Fort Collins, CO (US); Joseph C. Long, Olathe, KS (US)

(73) Assignee: ACT Holding, LLC, Olathe, KS (US)

( * ) Notice: Subject to any disclaimer, the term of this patent is extended or adjusted under 35 U.S.C. 154(b) by 0 days.

(21) Appl. No.: 16/154,238

(22) Filed: Oct. 8, 2018

(65) Prior Publication Data

US 2019/0038479 A1 Feb. 7, 2019

Related U.S. Application Data

(63) Continuation of application No. 15/682,701, filed on Aug. 22, 2017.
(Continued)

(51) Int. Cl.
*A61F 13/494* (2006.01)
*A61F 13/49* (2006.01)
(Continued)

(52) U.S. Cl.
CPC ........ *A61F 13/494* (2013.01); *A61F 13/4946* (2013.01); *A61F 13/49058* (2013.01);
(Continued)

(58) Field of Classification Search
CPC .... A61F 2013/49486; A61F 2013/5055; A61F 13/494; A61F 13/49058; A61F 13/539;
(Continued)

(56) References Cited

U.S. PATENT DOCUMENTS 4,961,736 A * 10/1990 McCloud .......... A61F 13/49004
604/385.15
6,926,705 B1 * 8/2005 Coates .................. A61F 13/495
604/385.14
(Continued)

FOREIGN PATENT DOCUMENTS

JP 2015126816 A * 7/2015
WO 2017115492 7/2017

OTHER PUBLICATIONS

MamaBanana's Adventures, "GMD Wprkhorse Fitted Review; Prepping Natural Fiber" Jan. 30, 2015. http://mamabananasadventures.com/workhorse-fitted-cloth-diaper-review.html. (Year: 2015).*

*Primary Examiner* — Tatyana Zalukaeva
*Assistant Examiner* — Gabriella E Burnette
(74) *Attorney, Agent, or Firm* — Hovey Williams LLP (57) ABSTRACT

A diaper insert has a liquid impermeable external surface, an inner surface, and an absorbency area adjacent the inner surface. The absorbency area has at least one absorbent layer. The diaper insert has a distal end, an attachment end, and a midsection between the distal end and attachment end. The midsection has opposing sides that are in general mirror images to one another about a vertical line. A width of the midsection is less than or equal to a width of the attachment end, and a width of the midsection is less than or equal to a width of the distal end.

30 Claims, 12 Drawing Sheets

Related U.S. Application Data (60) Provisional application No. 62/378,023, filed on Aug. 22, 2016.

(51) Int. Cl.
*A61F 13/539* (2006.01)
*A61F 13/74* (2006.01)
*A61F 13/505* (2006.01)

(52) U.S. Cl.
CPC ...... *A61F 13/49466* (2013.01); *A61F 13/505* (2013.01); *A61F 13/539* (2013.01); *A61F 13/74* (2013.01); *A61F 2013/49486* (2013.01)

(58) Field of Classification Search
CPC . A61F 13/49001; A61F 13/493; A61F 13/505
See application file for complete search history.

(56) References Cited

U.S. PATENT DOCUMENTS

| | | | | |
|---|---|---|---|---|
| 8,444,618 | B2* | 5/2013 | Kudo | A61F 13/47218 604/385.101 |
| 8,814,843 | B2* | 8/2014 | Van Bogart | A61F 13/15268 604/385.14 |
| 2005/0022291 | A1* | 2/2005 | Coates | A61F 13/49 2/400 |
| 2012/0116340 | A1* | 5/2012 | Labit | A61F 13/15268 604/377 |
| 2013/0006208 | A1* | 1/2013 | Close | A61F 13/471 604/385.09 |
| 2013/0274699 | A1* | 10/2013 | Kelley | A61F 13/505 604/385.09 |
| 2014/0221954 | A1* | 8/2014 | Wang | A61L 15/40 604/385.14 |
| 2016/0279001 | A1* | 9/2016 | Price | A61F 13/84 |
| 2018/0360673 | A1 | 12/2018 | Inoue et al. | |

* cited by examiner

UNDERGARMENT SYSTEM WITH ABSORBENT FLAP

RELATED APPLICATIONS

This is a continuation of prior application Ser. No. 15/682,701, filed Aug. 22, 2017, entitled DIAPER SYSTEM AND FLAP, which claims priority to U.S. Provisional Patent Application Ser. No. 62/378,023, filed Aug. 22, 2016, each of which is hereby incorporated in its entirety by reference herein.

FIELD OF THE INVENTION

The present invention relates to diaper systems and flaps. More specifically, the present invention relates to diaper systems and flaps designed to prevent leakage of bodily fluids.

BACKGROUND

Diaper systems have long been used with children as a way of containing urine and excrement before a child begins to use a toilet. Diapers contain absorbent material to prevent a wearer from soiling outer garments. Diapers may also be utilized by adults or adolescents who are unable to use a toilet or may be incontinent.

BRIEF SUMMARY OF THE INVENTION

The following presents a simplified summary in order to provide a basic understanding of some aspects of the invention. This summary is not an extensive overview of the invention. It is not intended to identify critical elements of the invention or to delineate the scope of the invention. Its sole purpose is to present some concepts of the invention in a simplified form as a prelude to the more detailed description that is presented elsewhere.

In one embodiment, a diaper system has a diaper having a front waist portion for being positioned proximate a wearer's abdominal area when fastened to the wearer and having a front edge, a rear waist portion having a rear edge, a central portion extending from the front waist portion to the rear waist portion, an interior surface, and an outer surface. The diaper system has a flap having an attachment end, a distal end, a midsection between the attachment end and the distal end, an inner surface, and an external surface. The attachment end is coupled to the outer surface. An absorbency area is adjacent the inner surface and has at least one absorbent layer. The midsection has a width that is less than or equal to a width of the distal end.

In another embodiment, a diaper insert has a liquid impermeable external surface, an inner surface, and an absorbency area adjacent the inner surface, the absorbency area having at least one absorbent layer configured to interact with an inner surface of the diaper to form a barrier restricting leakage of bodily fluids. The diaper insert has a distal end, an attachment end, and a midsection between the two. The diaper insert narrows from the attachment end to the midsection. The midsection has a width that is less than or equal to a width of the distal end.

In still another embodiment, an undergarment flap has an external surface, an inner surface adjacent an absorbency area, at least one absorbent layer adjacent the inner surface. The undergarment has an attachment end, a distal end, and a midsection between the attachment end and the distal end. The midsection has opposing sides that are generally mirror images to one another about a vertical line. A width of the midsection is less than or equal to a width of the attachment end and the width of the midsection is less than or equal to a width of the distal end.

In yet another embodiment, a method for minimizing leakage of bodily fluids from exiting a diaper system is provided. A diaper to be worn by a wearer is unfolded. The diaper has a front waist portion for being positioned proximate a wearer's abdominal area, the front waist portion has a front edge. The diaper has a rear waist portion having a rear edge and a central portion extending from the front waist portion to the rear waist portion. The diaper further has an interior surface and an outer surface. Then, a flap is coupled to the outer surface of the diaper. The flap has an attachment end, a distal end, and a midsection between the attachment end and the distal end. The flap further has an inner surface, an external surface, and an absorbency area adjacent the inner surface. The absorbency area has at least one absorbent layer. The flap is then folded up and over into the interior surface of the diaper to form a first fold. The flap is folded again at the midsection to create a folded area and an accordion fold. The flap is folded such that the distal end is proximate the attachment end, and is also proximate the diaper. Lastly, the diaper and the flap are secured to the wearer using side fasteners. The front edge forms a seal with the wearer's abdominal area, and the rear edge forms a seal with the wearer's lower back.

DETAILED DESCRIPTION

Figure 1:
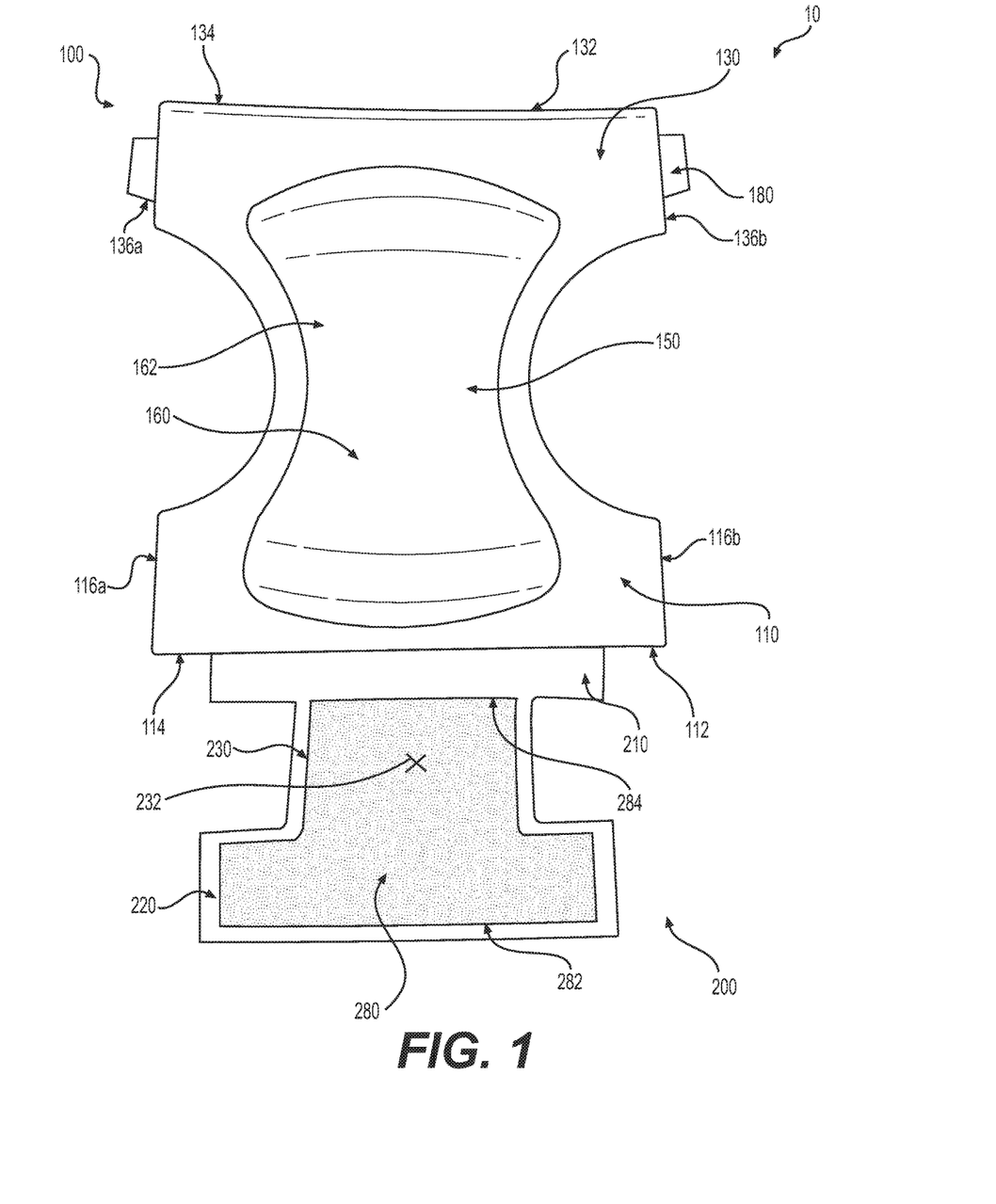
FIG. 1 is a top view of an unfolded diaper and flap according to an embodiment of the invention.

A diaper system 10 having a diaper 100 and a flap 200 may be configured to interact with a wearer to contain bodily fluids. The depicted diaper comprises a preferred undergarment 100. However, various aspects of the invention can be used in connection with other types of undergarments, such as training pants, pull-ups, underwear, boxers, or a garter. As shown in FIG. 1, the diaper 100 has a front waist portion 110, a rear waist portion 130, a central portion 150, an interior surface 160, and an outer surface 170. The flap 200 has a proximal attachment end 210, a distal end 220, and a midsection 230 between the attachment end 210 and distal end 220. The diaper 100 may generally have an hourglass-shaped planar configuration, as shown in FIG. 1.

The front waist portion 110 may have a front edge 112 defining a top of the front waist portion 114, and opposing sides 116a, 116b that are generally parallel to each other. The rear waist portion 130 has a rear edge 132 defining a top of the rear waist portion 134, and opposing sides 136a, 136b that are generally parallel to each other. The central portion 150 is between the front waist portion 110 and the rear waist portion 130. The front waist portion 110 may be positioned proximate the wearer's abdominal area when the diaper 100 is fastened to the wearer, and the rear waist portion 130 may be positioned proximate the wearer's lower back when the diaper 100 is fastened to the wearer.

Side fasteners 180 may be fixed to the rear waist portion 130 proximate each opposing side 136a, 136b. The side fasteners 180 may be used to attach the rear waist portion 130 to the front waist portion 110. When the side fasteners 180 are engaged, the diaper 100 may be secured to the wearer. The outer surface 170 of the diaper 100 is preferably liquid impermeable. The interior surface 160 may be absorbent, and may consist of at least one absorbent layer 162. The diaper 100 may be disposable, reusable, or constructed from such materials as nonwoven plastic or cotton.

The flap 200 is configured to be coupled to the diaper 100. The flap 200 may be releasably coupled to the diaper 100, or the flap 200 may be securely coupled to the diaper 100. Moreover, the flap 200 may be coupled at a waist band of other types of undergarments, such as training pants, pull-ups, underwear, boxers, or a garter.

Figure 2:
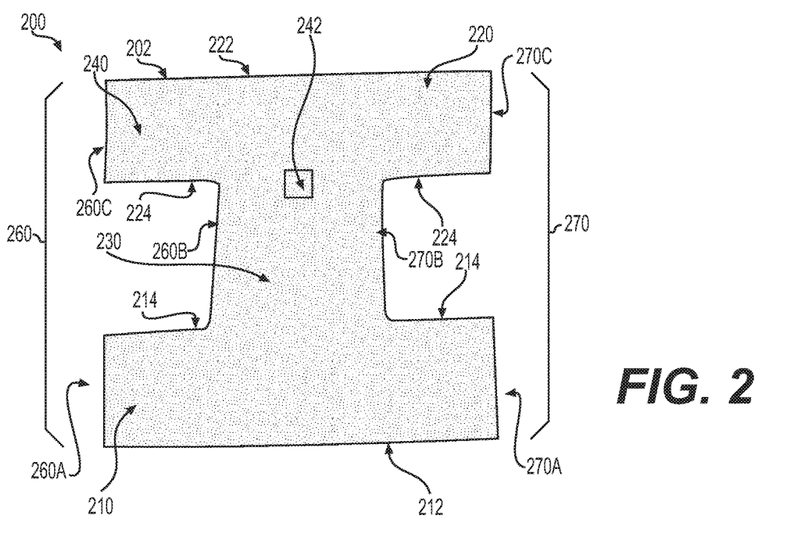
FIG. 2 is a bottom view of the flap of FIG. 1.
Figure 3:
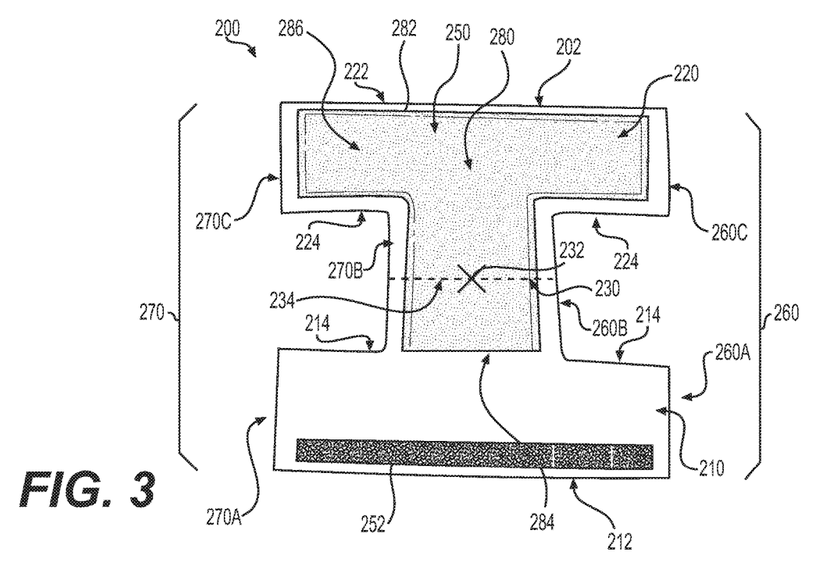
FIG. 3 is a top view of the flap of FIG. 1.
Figure 4:
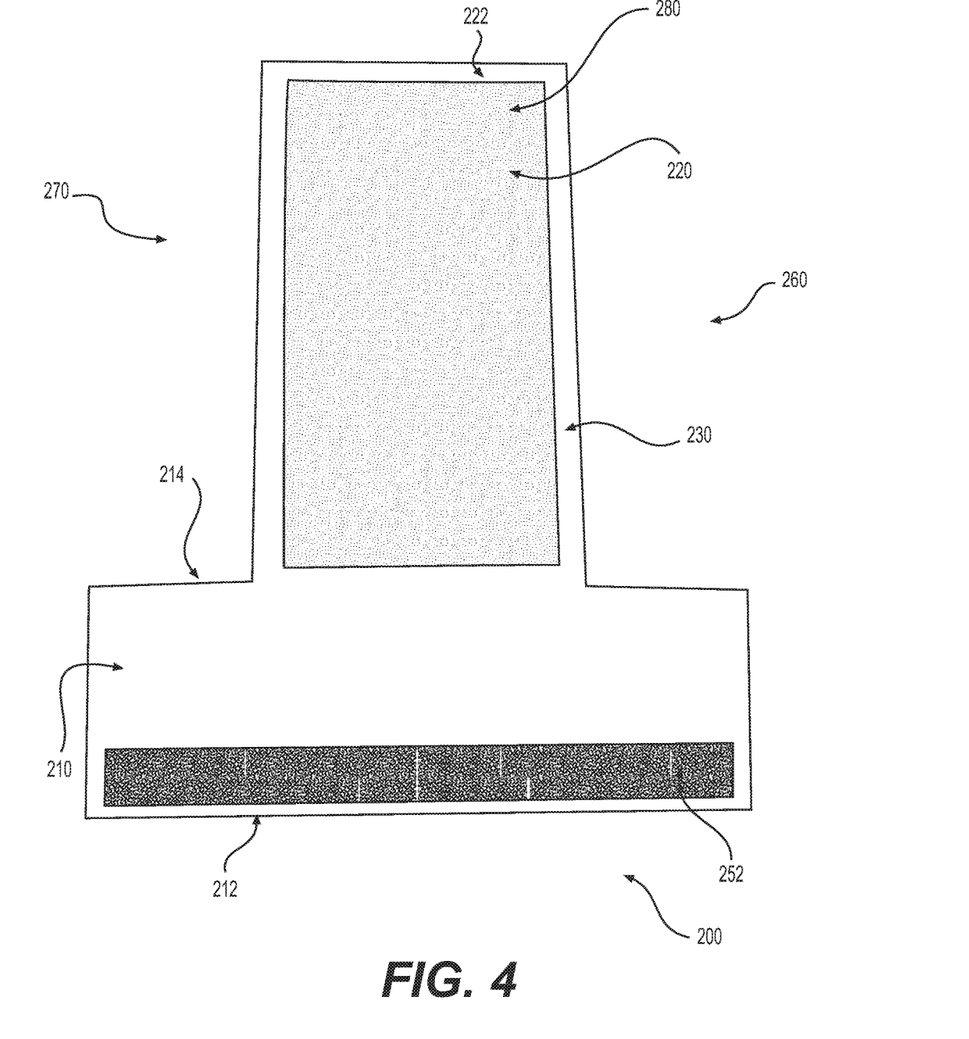
FIG. 4 is a T-shaped flap according to another embodiment of the invention.
Figure 5:
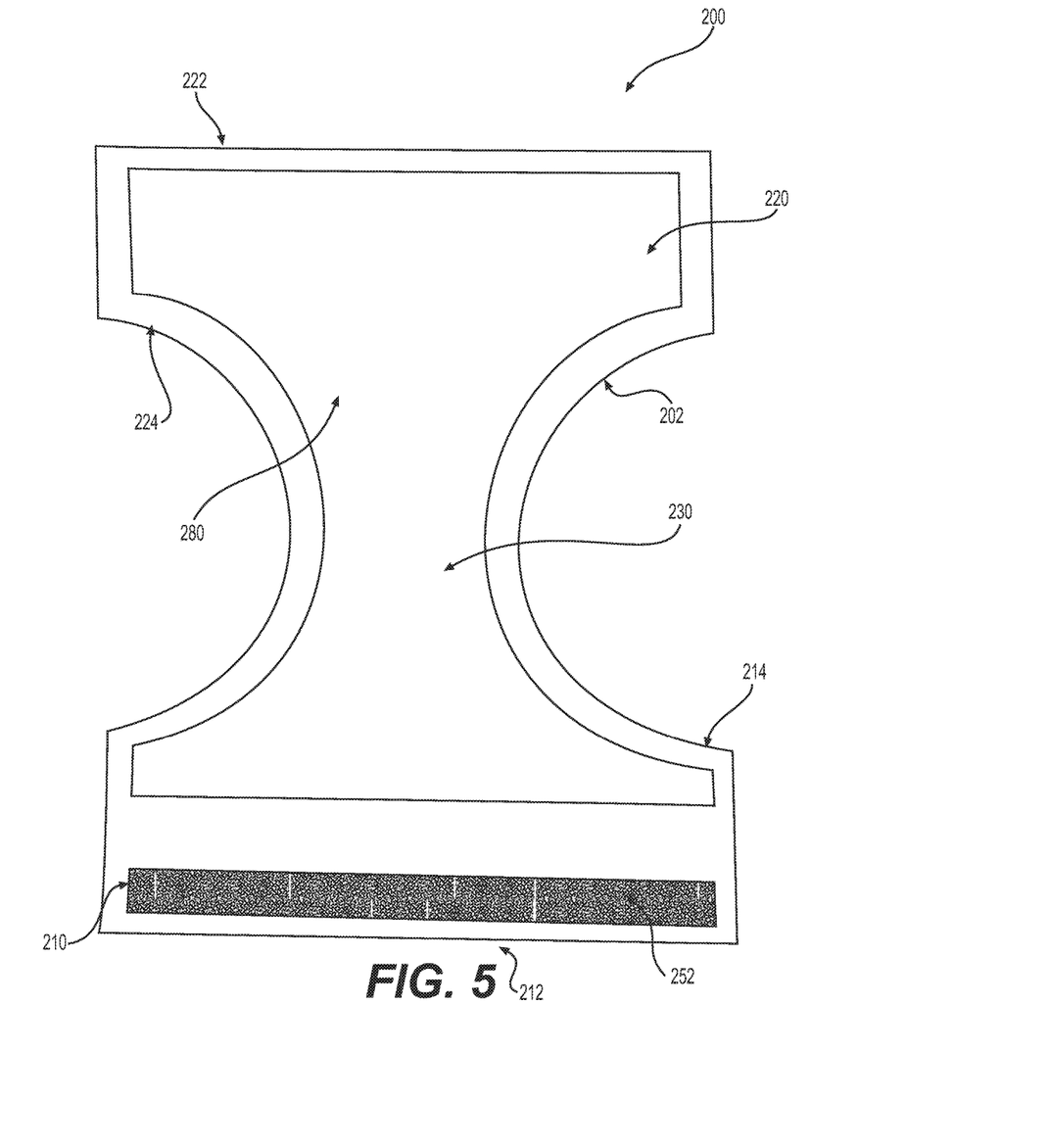
FIG. 5 is an hourglass-shaped flap according to still another embodiment of the invention.

As shown in FIG. 2 and FIG. 3, the attachment end 210 has an edge 212 and a boundary 214 at the midsection 230. The distal end 220 also has an edge 222 and a boundary 224 at the midsection 230. The midsection 230 has a center point 232 that may also be a center point between the distal end 220 and the attachment end 210. There may be a centerline (shown in a dashed line in FIG. 3) at the center point 232. The distal end 220 and the attachment end 210 may be mirror images of each other across the centerline. The flap 200 further has a first side 260 and a second side 270, with a vertical line (not shown) bisecting the flap 200 between the first side 260 and the second side 270. In some embodiments, the two sides 260, 270 may be substantially parallel to one another. Those skilled in the art will appreciate that the attachment end 210 and the distal end 220 may be any shape, including, but not limited to, a trapezoid, rectangle, triangle, and semi-circle. In some embodiments, the attachment end 210 and the distal end 220 may be shaped substantially similar, and may mirror one another. Those skilled in the art will also appreciate that the flap 200 may be any shape. FIG. 4 illustrates an embodiment of the flap 200 wherein the flap 200 is T-shaped. FIG. 5 illustrates an embodiment of the flap 200 wherein the flap 200 has a substantially hourglass configuration. In other embodiments, the flap 200 may be I-shaped, as is shown in FIG. 2 and FIG. 3. The attachment end 210 may have a width approximately equal to a width of the front edge 112.

In the I-shaped embodiments, and as shown in FIG. 2 and FIG. 3, the distal end 220 has a substantially similar width to a width of the attachment end 210. A first and second side 260a, 270a of the attachment end 210 may be generally parallel to one another. The sides 260a, 270a may extend from the edge of the attachment end 212 to the boundary of the attachment end 214. The boundary of the attachment end 214 may be generally parallel with the edge of the attachment end 212, and may form a perpendicular angle with the sides 260a, 270a. The attachment end boundary 214 may abut the midsection 230. In some embodiments, the attachment end boundary 214 may be perpendicular to the midsection 230. A width of the midsection 230 may be defined by a first side 260b and a second side 270b of the midsection 230. A first and second side 260b, 270b of the midsection 230 may be parallel to one another throughout the midsection 230. The midsection 230 may abut the distal end boundary 224, which may extend parallel to the edge of the distal end 222. A first and second side 260c, 270c of the distal end 220 may extend at a perpendicular angle from the distal end boundary 214 toward the edge of the distal end 212, and may be generally parallel each other.

In some embodiments, a width of the flap 200 is the smallest between opposing sides 260b, 270b of the midsection 230. The width of the flap 200 may vary at different areas of the flap 200. The width of the flap 200 may narrow from the attachment end 210 toward the midsection 230. The width of the flap 200 may similarly narrow from the distal end 220 toward the midsection 230. The width of the flap 200 at the midsection 230 may be less than or equal to a width of the central portion 150 of the diaper 100. In some embodiments, the width of the midsection 230 is less than or equal to the width of the distal end 220. In other embodiments, the width of the midsection 230 is less than or equal to the width of the attachment end 210.

The flap 200 has an external surface 240 and an inner surface 250. The external surface 240 may be liquid impermeable. In some embodiments, for aesthetic purposes, the external surface 240 may have a pattern or other artistic decoration. Further, the external surface 240 may have a wetness indicator. The external surface 240 may have an adhesion area 242 (shown in FIG. 2), and those skilled in the art will appreciate that the adhesion area 242 may utilize an adhesive material, glue, zipper, hook and loop fasteners, or other methods of attachment now known or later discovered. In some embodiments, the adhesion area 242 may utilize a pressure sensitive adhesive material proximate the distal end boundary 224. The adhesion area 242 may be at or proximate to the midsection 230. In some embodiments, the adhesion area 242 may be at the distal end boundary 224 or the attachment end boundary 214. In other embodiments, the adhesion area 242 may be proximate the edge 222 of the distal end 220. The external surface 240 may be secured to itself at the adhesion area 242. The flap 200 would still be able to move relative the adhesion area 242, and the adhesion area 242 may not restrict movement. In some embodiments, the adhesion area 242 is proximate the distal end boundary 224 and adheres to the external surface 240 at the attachment end boundary 214.

The inner surface 250 may be absorbent. In some embodiments, for aesthetic purposes, the inner surface 250 may have a pattern or other artistic decoration. Further, the inner surface 250 may have a wetness indicator. The inner surface 250 may have at least one attachment area 252 proximate the attachment end 210 of the flap 200. The attachment area 252 may be configured to be coupled to the outer surface 170 of the diaper 100. Those skilled in the art will appreciate that the attachment area 252 may utilize an adhesive material, zipper, hook and loop fasteners, safety pins, plastic rivets, roll on glue, or other methods of attachment now known or later discovered. Further, the outer surface 170 of the diaper 100 may be configured to interact with the attachment area 252, and may also utilize an adhesive material, zipper, hook and loop fasteners, or other methods of attachment now known or later discovered. In some embodiments, the attachment area 252 may have a strip of pressure sensitive adhesive material that may be used to couple the flap 200 to the diaper 100. In other embodiments, the attachment area 252 may extend a width of the attachment end 210. In still other embodiments, the flap 200 has multiple attachment areas 252. In some embodiments, the side fasteners 180 may be utilized to secure the flap 200 to the diaper 100. Alternately, the flap 200 may be secured to the outer surface 170 by an adhesive material.

The attachment area 252 may be configured to couple to the outer surface 170 proximate the front waist portion 110. The attachment area 252 may be coupled to the outer surface 170 proximate the front edge 112, and may extend a width of the front edge 112. In other embodiments, the flap 200 may be configured to be coupled to the outer surface 170 of the diaper 100 proximate the rear waist portion 130, and may further be coupled proximate the rear edge 132.

It is foreseeable that the flap 200 may be permanently fixed from the attachment end 210 to the outer surface 170 at the front waist portion 110 of the diaper 100. The diaper 100 and flap 200 may be a single, unitary construction. In those embodiments, the attachment area 252 and the outer surface 170 of the diaper 100 may be indistinguishable and the flap 200 may extend from the front edge 112. In this configuration, when in use, the flap 200 may not extend up and over the top 114 of the diaper 100, but may extend downward towards the central portion 150 of the diaper 100.

Figure 6:
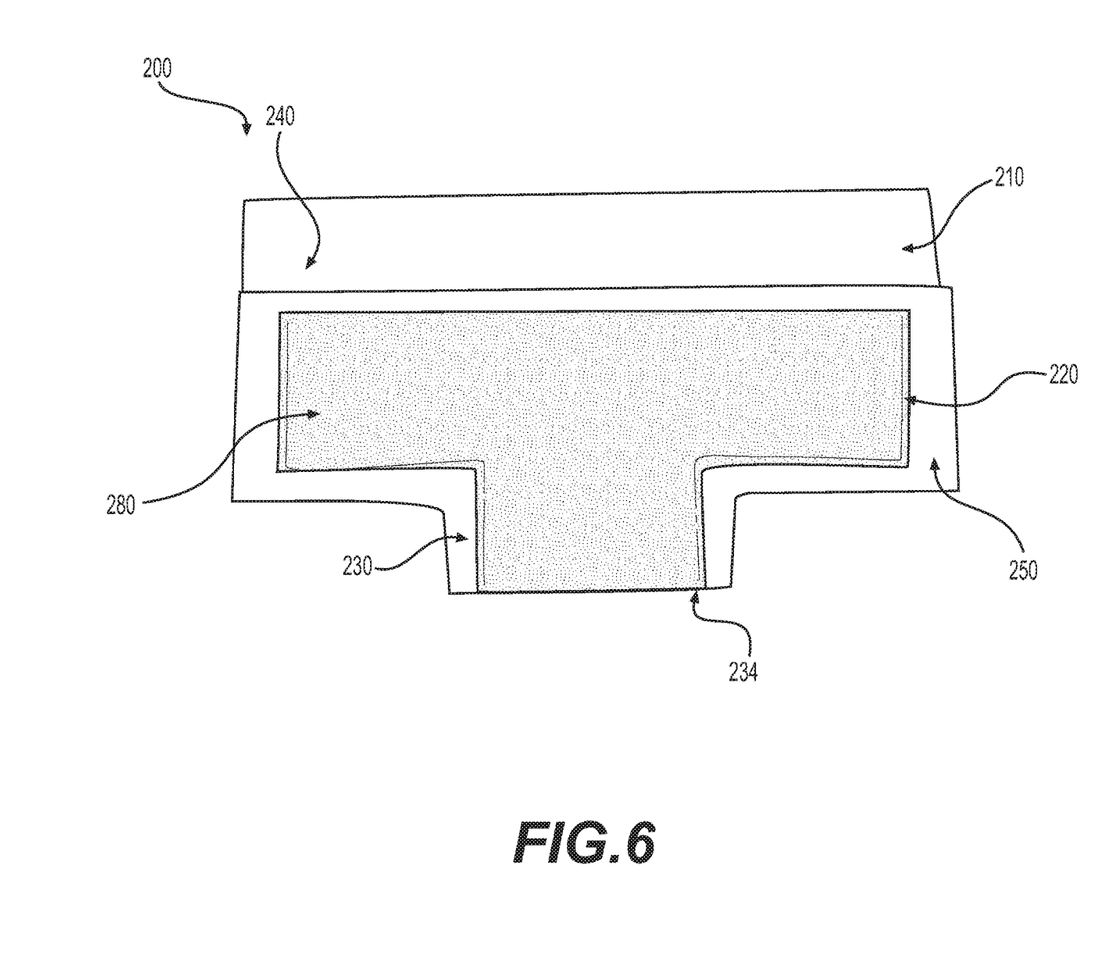
FIG. 6 is a front view of the flap of FIG. 1 in a folded configuration.

The flap 200 may have a planar configuration and a folded configuration (see FIG. 6). The flap 200 may be provided in either configuration. In the folded configuration, the flap 200 may be folded at the midsection 230 forming a folded area 234, which may act as a barrier. The flap 200 may be folded proximate the center point 232 and, the inner surface 250 may be generally exposed, as is shown in FIG. 6. In the folded configuration, the distal end 220 may be proximate the attachment end 210. In some embodiments, the distal end 220 may also be proximate the front edge 112. In the folded configuration and when coupled to the outer surface 170 of the diaper 100, the flap 200 may form a Z-fold, as the flap 200 may be folded at a front edge 112 or rear edge 132 of the diaper 100, and again at the folded area 234. In other embodiments, the flap 200 could further be folded, creating a W-fold, or other accordion type folds.

At least a portion of the inner surface 250 is adjacent to an absorbency area 280. An area of the absorbency area 280 may be more than half an area of the inner surface 250. In some embodiments, the area of the absorbency area 280 may be generally similar (and in some embodiments, identical) to the entire area of the inner surface 250. In other embodiments, the absorbency area 280 may be adjacent to the inner surface 250 except for a boundary of one half inch or less from an outer perimeter 202 of the flap 200 (see FIG. 3). The outer perimeter 202 of the flap 200 may be sealed against leakage such that the absorbency area 280 is secured. The outer perimeter 202 may be crimped, bonded, heat sealed, or sealed with another method now known or later discovered. In some embodiments, the edge of the distal end 224 may be sealed against leakage, and may further have a water impermeable coating. In some embodiments, excess material from the outer surface 240 may extend up and over the edge 224 of the distal end 220 such that the distal end 220 is sealed against leakage. In other embodiments, the absorbency area 280 may be adjacent to the distal end 220 and the midsection 230. A first end of the absorbency area 282 may be proximate the edge of the distal end 222, and a second end 284 may be proximate the boundary of the attachment end 214. In other embodiments, the absorbency area 280 continues into the attachment end 210. A width of the absorbency area 280 at the attachment end 210 may be equal to or less than a width of the absorbency area 280 at the midsection 230.

The absorbency area 280 has at least one absorbent layer 286. The absorbent layer 286 may help to absorb bodily fluids, and may expand and aid in restricting leakage. The absorbent layer 286 is positioned between the attachment end 210 and the distal end 220. The absorbent layer 286 may extend a width of the flap 200. Alternately, the absorbent layer 286 may extend a length of the flap 200. In some embodiments, the absorbent layer 286 extends a width of the distal end 220. The absorbent layer 286 may be configured to expand in an accordion-like fashion.

There may be different numbers of absorbent layers 286 at different parts of the absorbency area 280. In some embodiments, there are additional absorbent layers 286 proximate the distal end 220. In other embodiments, there are additional absorbent layers 286 proximate the midsection 230, and the absorbent layers 286 may be further increased at the folded area 234. The absorbency area 280 may have multiple absorbent layers 286 which may each be composed of a different material. It may be beneficial to have additional absorbent layers 286 at the distal end 220, as well as additional absorbent layers 286 at the midsection 230. Further, there may be additional absorbent layers 286 at a first end 284 of the absorbency area 280. The placement of the absorbent layer 286 may assist in efficiently pushing liquid toward areas that have not yet absorbed liquid. In this regard, the combination of the diaper 100 and the flap 200 may increase the overall efficiency and absorbency when compared to an absorbency of a standard diaper 100. In some embodiments, the absorbent layer 286 may be configured to expand in an accordion-like fashion. Those skilled in the art will appreciate that the absorbent layer 286 may consist of absorbent gel, super absorbent polymers, absorbent fibers, wood pulp, or any other absorbent material now known or later discovered.

Figure 7:
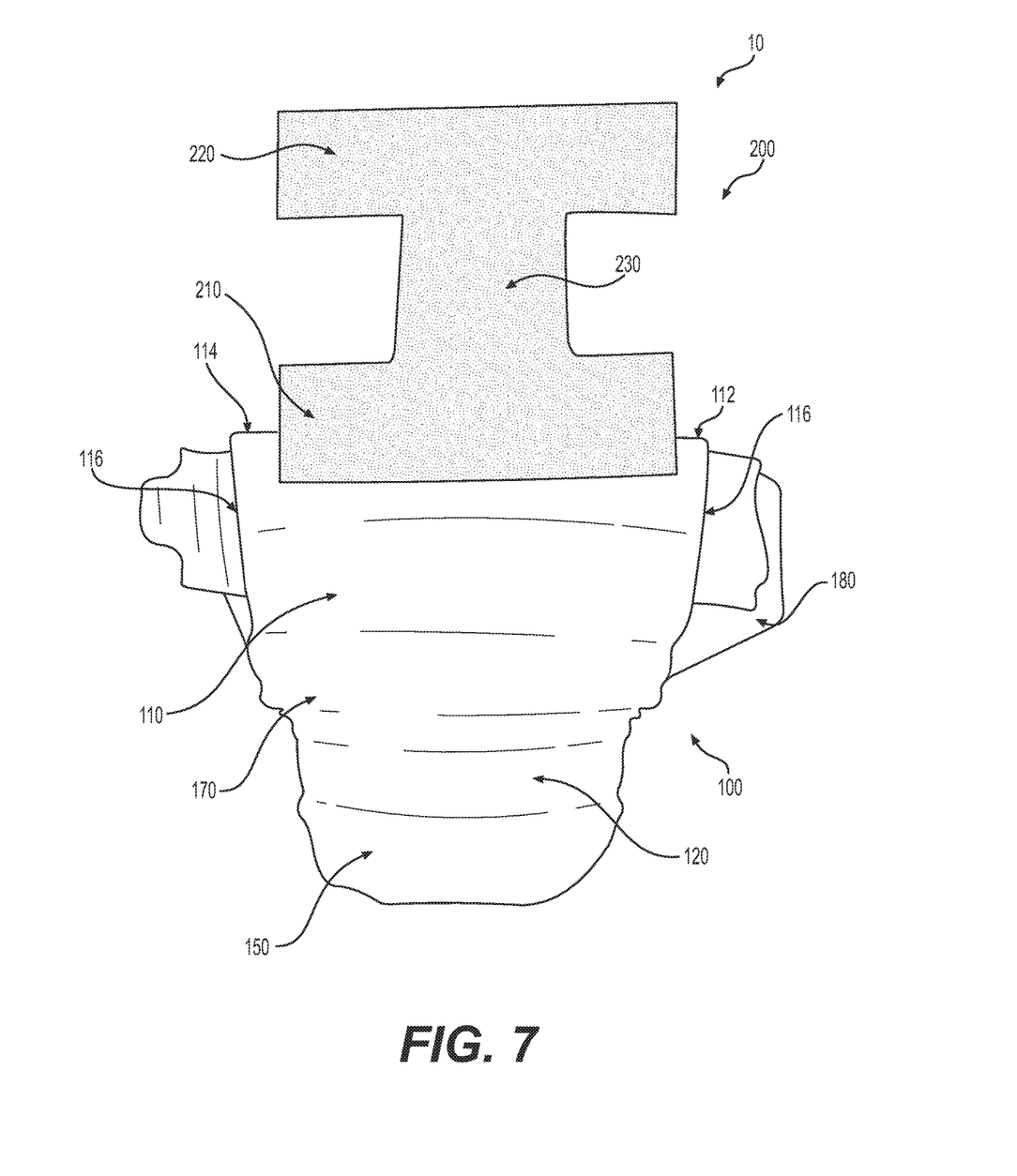
FIG. 7 is a front view of the diaper and the flap of FIG. 1, with the flap coupled to the diaper.
Figure 8:
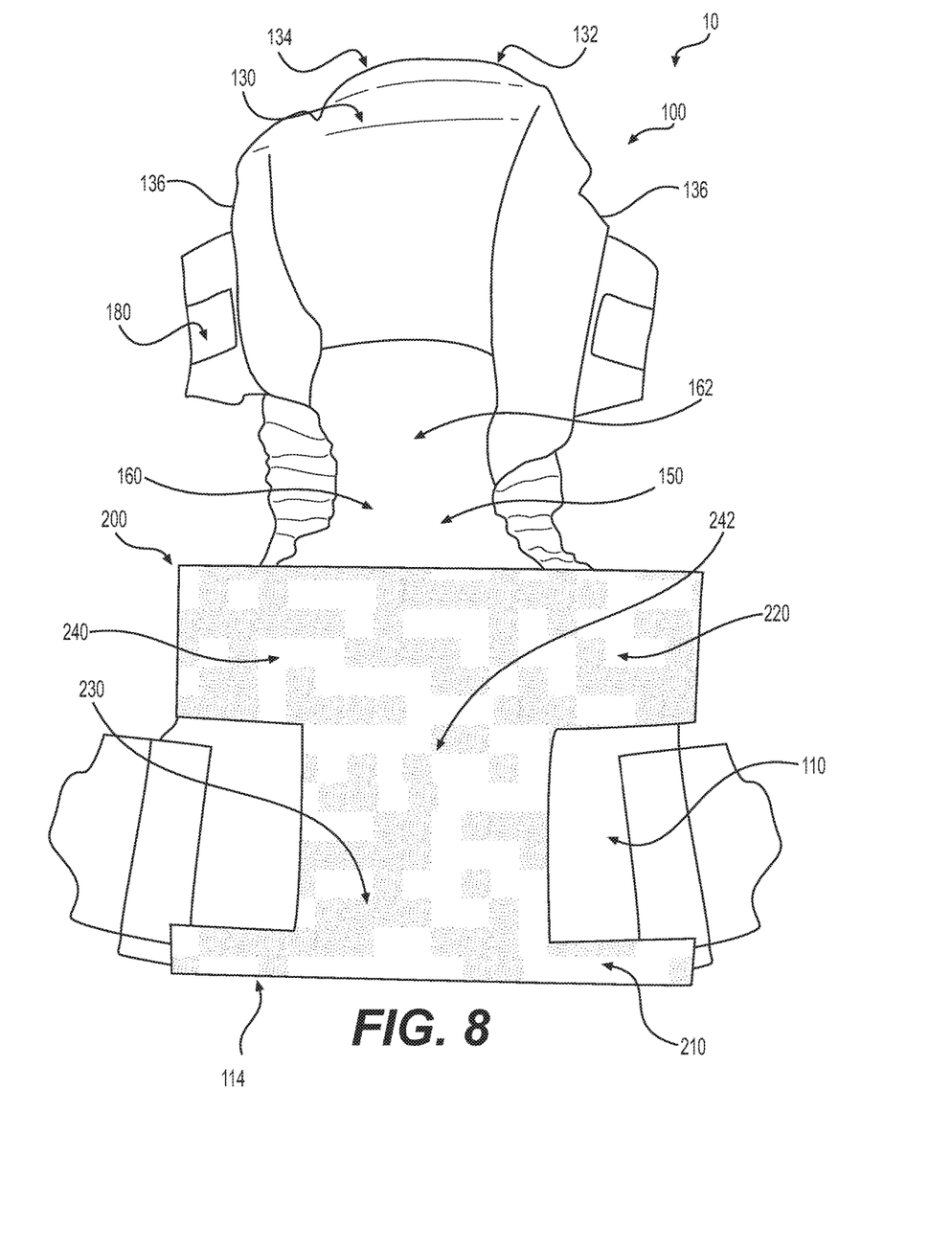
FIG. 8 is a top view of the diaper and the flap of FIG. 1, with the diaper open and the flap folded toward the diaper.
Figure 9:
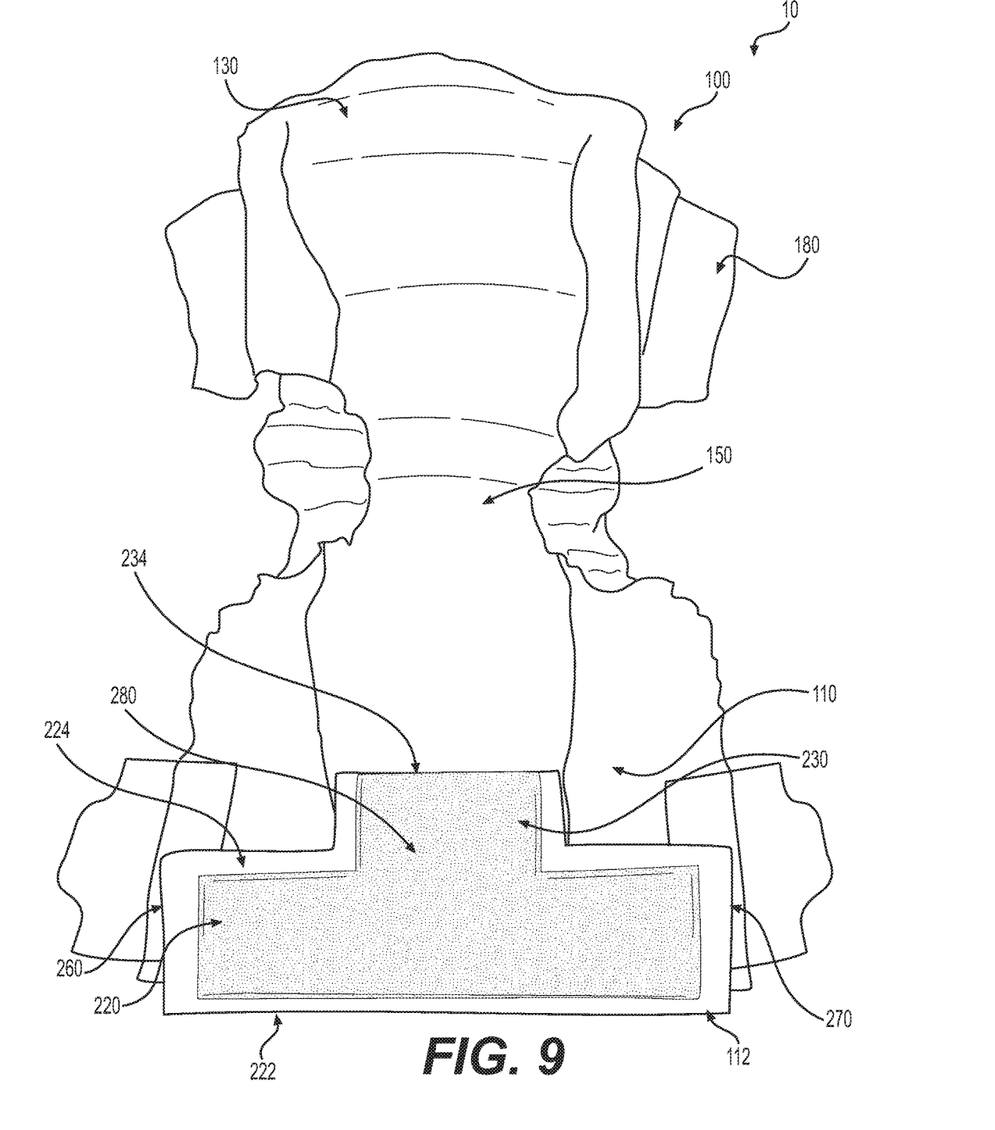
FIG. 9 is a top view of the diaper and the flap of FIG. 1, with the diaper open and the flap at the folded configuration of FIG. 6.
Figure 10:
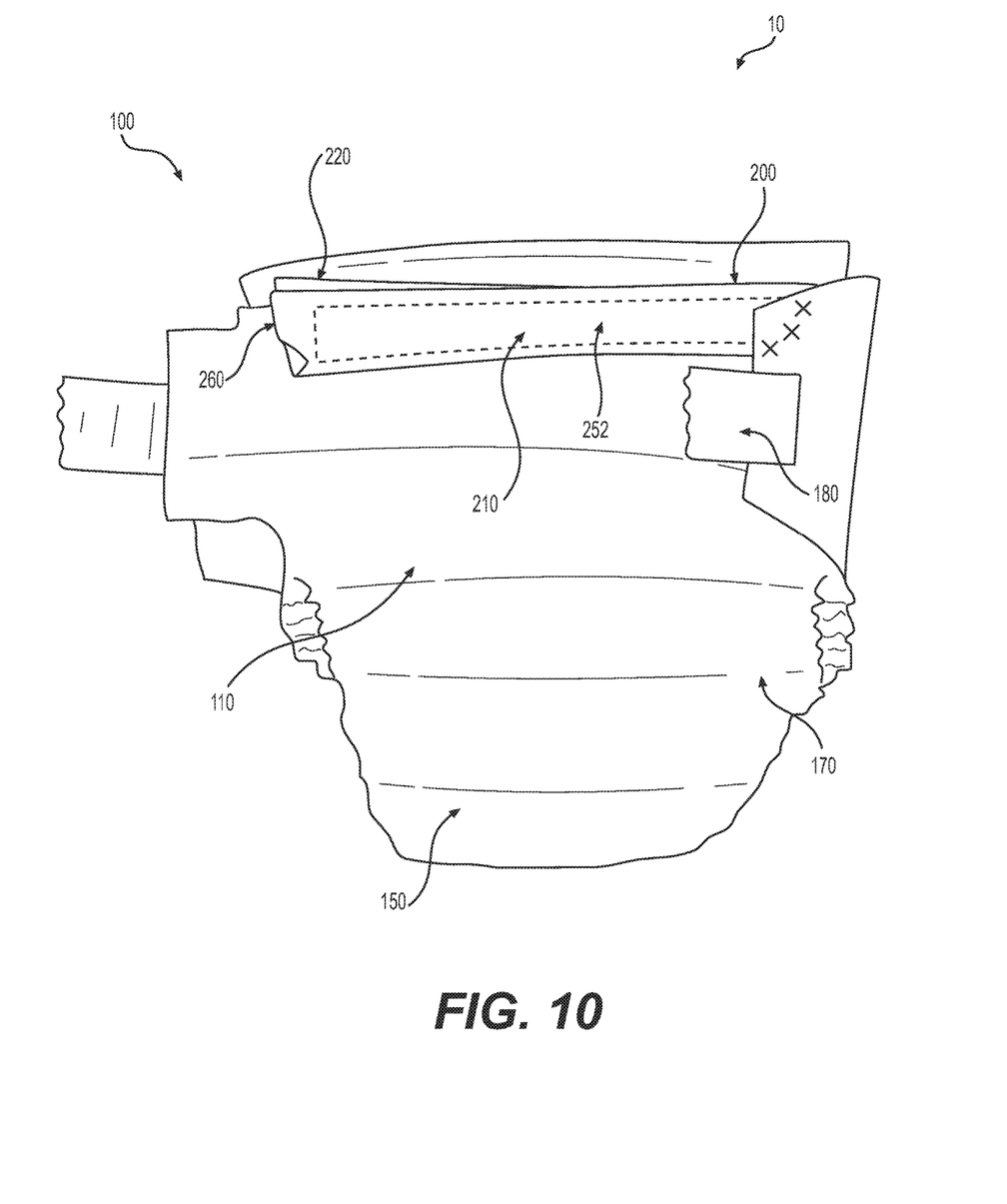
FIG. 10 is a front view of the diaper and the flap of FIG. 1, showing the outer surface of the diaper with the flap folded into the diaper.

In some embodiments, and as shown in FIG. 7, the flap 200 may be configured to be coupled to the outer surface 170 of the diaper 100 proximate the front edge 112. Coupling the flap 200 to the diaper 100 may aid in minimizing leakage. Further, the flap 200 may act as a barrier and provide additional absorbency. The flap 200 may already be in a folded configuration, or the flap 200 may be substantially planar. As shown in FIG. 8, the flap 200 may be coupled proximate the front edge 112, and may then be folded up and over the top 114 of the front waist portion 110 and into the diaper 100, forming an upper fold 290 (see FIGS. 12 and 13). The flap extends downwardly from the upper fold 290 along the interior surface 160. The flap 200 may extend along the interior surface 160 of the diaper 100 from the front edge 112 to the rear edge 132. If the flap 200 is not in the folded configuration, the flap 200 may then be folded at the midsection 230 to create the folded area 234, as is shown in FIG. 9. In the folded configuration, the distal end 220 may be proximate the attachment end 210, and proximate the front edge 112. The external surface 240 may be secured to itself at the adhesion area 242 to ensure that the folded configuration is maintained. The flap 200 may have a Z-fold, as it may be folded up and over the top 114 of the front waist portion 110, and folded again at the folded area 234. Therefore, the flap 200 may be configured to expand in an accordion-like fashion. The inner surface 250 may be exposed to the wearer. Alternately, the flap 200 may be coupled to the interior surface 160. Once the flap 200 is coupled to the diaper 100 and in the folded configuration, the diaper 100 may be worn by the wearer (see FIG. 10 and FIG. 11, the wearer not shown for clarity).

In some embodiments, the flap 200 is reusable. The absorbency area 280 may be configured to be detached and replaced after each use. Alternately, the absorbent layer 286 may be configured to be detached and replaced after each use. Those skilled in the art can appreciate that the absorbency area 280 may be coupled to the flap 200 with an adhesive material, zipper, hook and loop fasteners, or other methods of attachment now known or later discovered. Alternately, the flap 200 may have an insert (not shown) configured to receive the absorbency area 280.

In some embodiments, the flap 200 may be provided by itself, as it may be beneficial for a user to attach the flap 200 to a diaper 100 instead of purchasing diaper systems 10 that have the flap 200 pre-coupled to the diaper 100. A diaper insert and an undergarment flap are substantially similar to the flap 200 as described above, except they are not coupled to the diaper 100.

When in use, the diaper 100 is secured to the wearer. The front edge 112 may be proximate an abdominal area of the user, and the rear edge 132 may be proximate a lower back of the user. The front waist portion 110 may be secured to the wearer such that the front edge 112 may form a seal with the wearer's abdominal area. Likewise, a rear waist portion 130 may be secured to the wearer such that the rear edge 132 may form a seal with the wearer's lower back. When the diaper 100 is secured to the wearer and the wearer shifts positions, it is foreseeable that the changing positions may cause gaps between the wearer and the diaper 100. For example, if the wearer were to place his legs over his head, or sleep on his stomach, this may cause a gap between the front edge 112 and the wearer. The flap 200 may allow the wearer to move more freely while the diaper system 10 maintains leakage protection.

Figure 11:
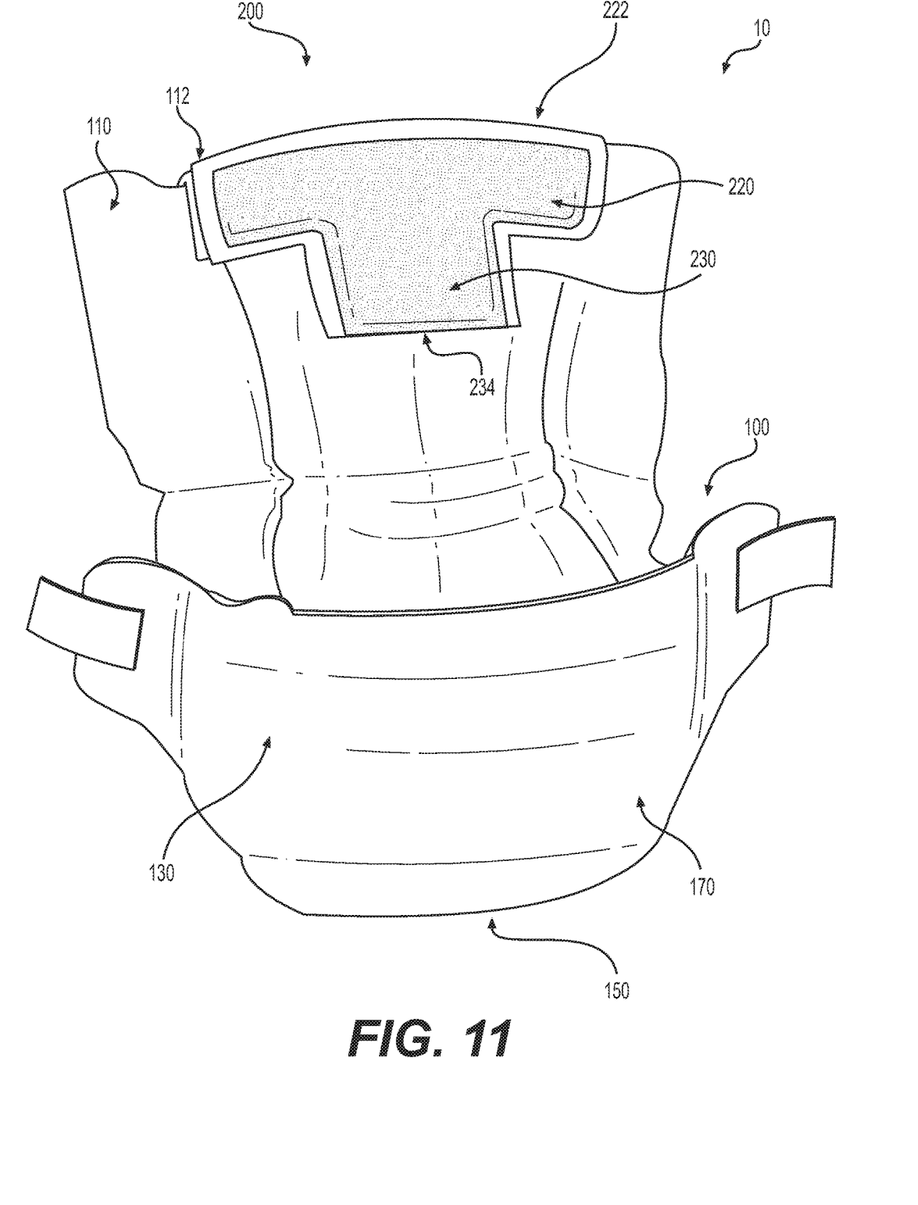
FIG. 11 is top view of FIG. 10, showing an interior of the diaper with the flap coupled to the diaper.

In use, the flap 200 may be attached to the diaper 100 and may be folded at the folded area 234. The folded area 234 may form a barrier between male genitalia of the wearer. The folded area 234 may be positioned below a waist of the wearer. A distal end 220 may be proximate the front edge 112 as shown in FIG. 11, and if the diaper 100 is fastened to the wearer, the front edge 112 may be secured tightly enough to the wearer such that the distal end 220 is held in place proximate the wearer's abdominal area. The distal end 220 may form a barrier proximate the front edge 112 such that fluids may be restricted from flowing upwards and out of the front edge 112 of the diaper 100. Similarly, if the flap 200 is coupled proximate the rear edge 132, the distal end 220 may form a barrier proximate the rear edge 132 such that fluids may be restricted from flowing upwards and out of the rear edge 132 of the diaper 100.

Figure 12:
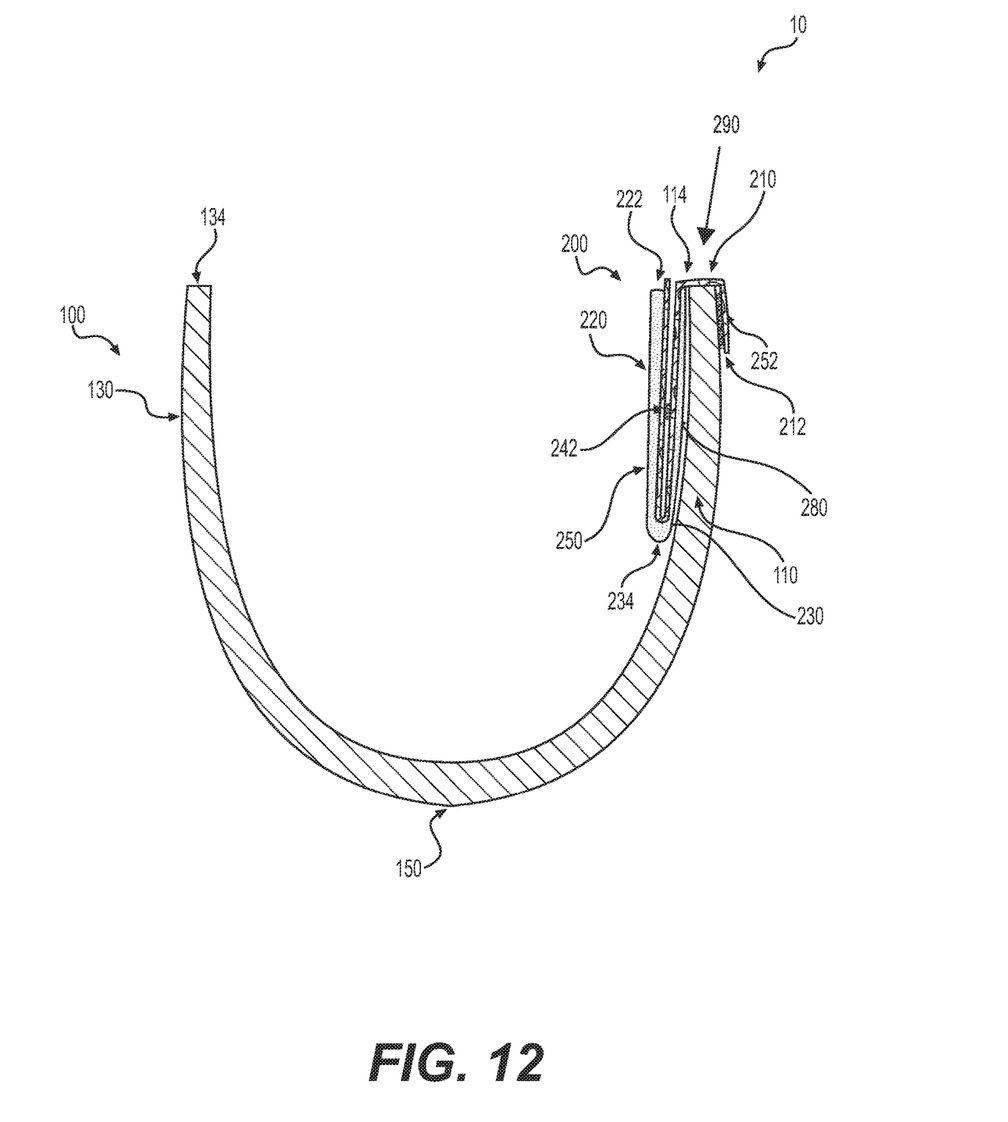
FIG. 12 is a cross sectional view of one embodiment of the diaper and flap of FIG. 1 at a dry use configuration.
Figure 13:
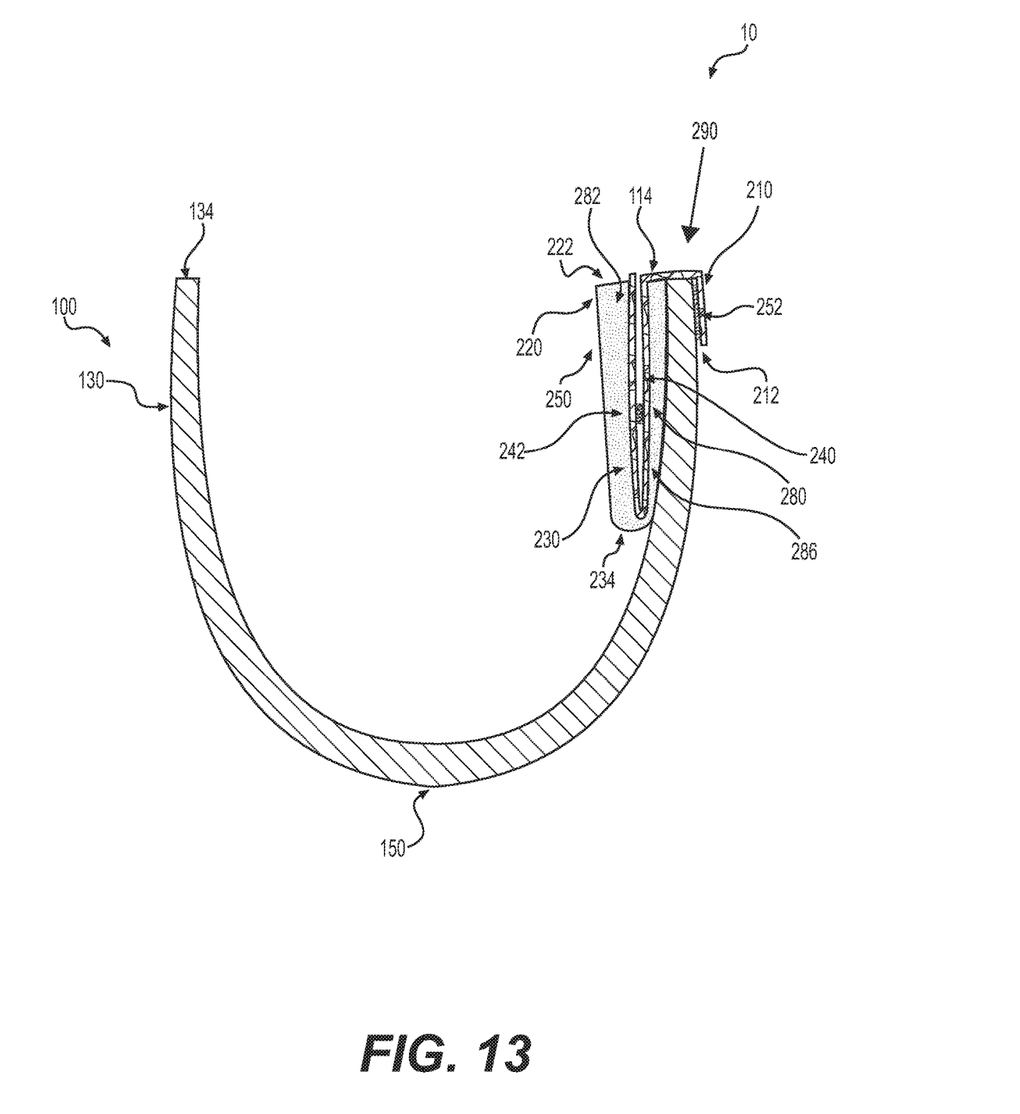
FIG. 13 is a cross sectional view of one embodiment of the diaper and the flap of FIG. 1, with an absorbency area of the flap expanded.

The flap 200 may be used with both male and female users. Male children may more easily urinate towards a front waist portion 110, and the urine may flow over the top 114 and out of the diaper 100. The flap 200 may be positioned to assist in restricting leakage, as is illustrated in FIG. 12. Often, a penis may be pointed in a downward position when a new diaper 100 is put on to attempt to prevent leakage and keep bodily fluids focused towards the central portion 150. However, the penis can easily shift to an upwards position, whereby bodily fluids may flow toward the front waist portion 110. The flap 200 may be positioned to absorb excess liquids proximate the front edge 112 and at the folded area 234. In addition to acting as a barrier, the flap 200 may assist in directing liquid towards areas of the flap 200 and diaper 100 that have not yet absorbed liquid, and may thereby increase the effectiveness of the diaper 100 to absorb liquid. The absorbency area 280 may be configured to receive urine from the wearer that may be relieving his bladder towards a front waist portion 110 of the diaper 100. As is shown in FIG. 13, the absorbency area 280 may expand as it absorbs liquid, and may assist to preventing leakage. The barrier may be formed at the top 114 of the front waist portion 110 of the diaper 100.

Many different arrangements are possible without departing from the spirit and scope of the present invention. Embodiments of the present invention are described herein with the intent to be illustrative rather than restrictive. Alternative embodiments will become apparent to those skilled in the art that do not depart from its scope. A skilled artisan may develop alternative means of implementing the disclosed improvements without departing from the scope of the present invention. Further, it will be understood that certain features and subcombinations are of utility and may be employed without reference to other features and subcombinations and are contemplated within the scope of the invention. The description should not be restricted to the specific described embodiments.

What is claimed is:

1. An undergarment system operable to be removably worn by a wearer, said undergarment system comprising:
   an undergarment including opposite front and rear waist portions and a central portion located between the front and rear waist portions, with the front and rear waist portions presenting front and rear edges, respectively,
   said undergarment presenting an interior surface that generally defines an undergarment interior when the undergarment is worn; and
   an absorbent flap including an absorbent flap layer and presenting an inner surface,
   said flap being attached directly to a respective waist portion to at least in part define an upper fold extending above the respective waist portion, with the flap extending downwardly from the upper fold along the interior surface of the undergarment such that the absorbent flap layer is positioned within the undergarment interior and at least part of said inner surface of the flap faces the interior surface of the undergarment.

2. An undergarment system as claimed in claim 1,
   said undergarment and said flap cooperatively forming a single, unitary construction.

3. An undergarment system as claimed in claim 1,
   said flap including an attachment element engaged with the undergarment to attach the flap to the undergarment.

4. An undergarment system as claimed in claim 3,
   said flap presenting a proximal end adjacent said respective edge and a midsection projecting from the proximal end,
   said attachment element being located along the proximal end.

5. An undergarment system as claimed in claim 4,
   said absorbent flap layer extending along the midsection.

6. An undergarment system as claimed in claim 3,
   said absorbent flap presenting an external surface opposite the inner surface, with at least part of the absorbent flap layer being located between the surfaces,
   said external surface at least along the upper fold being liquid impermeable to restrict fluid leakage out of the undergarment interior.

7. An undergarment system as claimed in claim 3,
   said undergarment presenting an exterior surface opposite the interior surface, said flap presenting a proximal end adjacent said respective edge,
said proximal end extending over the respective edge to the exterior surface, such that the flap forms the upper fold and a portion of the inner surface faces the exterior surface of the undergarment,
said attachment element being located along said portion of the inner surface.

8. An undergarment system as claimed in claim 3,
said flap projecting from said respective edge to a location spaced therefrom,
said location including the absorbent flap layer so as to form a barrier operable to block fluid flow toward said respective edge.

9. An undergarment system as claimed in claim 8,
said flap presenting proximal and distal ends and including a midsection extending between the proximal and distal ends,
said absorbent flap layer extending along at least part of the midsection,
said flap being folded at the location to form a midsection fold, with the barrier being defined by the midsection fold.

10. An undergarment system as claimed in claim 9,
said inner surface of the flap presenting oppositely facing first and second portions extending from the midsection fold, with the first portion facing the interior surface of the undergarment and the second portion facing the wearer when the system is worn,
said first and second portions of the inner surface being liquid permeable adjacent the midsection fold.

11. An undergarment system as claimed in claim 8,
said flap including a midsection projecting from the proximal end, with the width of the flap adjacent the proximal end being greater than the width of the midsection.

12. An undergarment system as claimed in claim 3,
said flap presenting a proximal end adjacent said respective edge,
said flap including a midsection projecting from the proximal end, with the width of the flap adjacent the proximal end being greater than the width of the midsection.

13. An undergarment system as claimed in claim 1,
said undergarment presenting an exterior surface opposite the interior surface,
said flap presenting a proximal end and a midsection projecting from the proximal end,
said proximal end extending over the respective edge to the exterior surface, such that the flap forms the upper fold and the midsection extends into the undergarment interior.

14. An undergarment system as claimed in claim 13,
said flap including an attachment element located along the proximal end,
said attachment element being engaged with the exterior surface of the undergarment to attach the flap thereto.

15. An undergarment system as claimed in claim 1,
said absorbent flap presenting an external surface opposite the inner surface, with at least part of the absorbent flap layer being located between the surfaces,
said external surface at least along the upper fold being liquid impermeable to restrict fluid leakage out of the undergarment interior.

16. An undergarment system as claimed in claim 1,
said undergarment presenting an exterior surface opposite the interior surface,
said flap presenting a proximal end adjacent said respective edge,
said proximal end extending over the respective edge to the exterior surface, such that the flap forms the upper fold and a portion of the inner surface faces the exterior surface of the undergarment.

17. An undergarment system as claimed in claim 1,
said flap projecting from said respective edge to a location spaced therefrom,
said location including the absorbent flap layer so as to form a barrier operable to block fluid flow toward said respective edge.

18. An undergarment system as claimed in claim 17,
said flap presenting proximal and distal ends and including a midsection extending between the proximal and distal ends,
said absorbent flap layer extending along at least part of the midsection,
said flap being folded at the location to form a midsection fold, with the barrier being defined by the midsection fold.

19. An undergarment system as claimed in claim 18,
said inner surface of the flap presenting oppositely facing first and second portions extending from the midsection fold, with the first portion facing the interior surface of the undergarment and the second portion facing the wearer when the system is worn,
said first and second portions of the inner surface being liquid permeable adjacent the midsection fold.

20. An undergarment system as claimed in claim 18,
said absorbent flap presenting an external surface opposite the inner surface, with at least part of the absorbent flap layer being located between the surfaces,
said external surface presenting opposed first and second portions extending from the midsection fold,
said first and second portions of the external surface being attached to one another to maintain the midsection fold.

21. An undergarment system as claimed in claim 20,
said absorbent flap including an adhesion area between the first and second portions of the external surface.

22. An undergarment system as claimed in claim 18,
said flap presenting a width that varies between the proximal and distal ends, with the width of the midsection being relatively smaller than the width of at least one of the ends.

23. An undergarment system as claimed in claim 22,
said proximal and distal ends presenting a substantially similar width,
said proximal and distal ends being adjacent one another.

24. An undergarment system as claimed in claim 17,
said flap presenting a proximal end adjacent said respective edge,
said flap including a midsection projecting from the proximal end, with the width of the flap adjacent the proximal end being greater than the width of the midsection.

25. An undergarment system as claimed in claim 17,
said absorbent flap presenting an external surface opposite the inner surface, with at least part of the absorbent flap layer being located between the surfaces,
said external surface at least along the upper fold being liquid impermeable to restrict fluid leakage out of the undergarment interior.

26. An undergarment system as claimed in claim 1,
said flap presenting a proximal end adjacent said respective edge, said flap including a midsection projecting from the proximal end, with the width of the flap adjacent the proximal end being greater than the width of the midsection.

27. An undergarment system as claimed in claim 26,
said flap presenting a distal end, with the midsection extending between the proximal and distal ends,
said flap being folded along the midsection to form a midsection fold,
said proximal and distal ends presenting a substantially similar width.

28. An undergarment system as claimed in claim 27,
said proximal and distal ends being adjacent one another.

29. An undergarment system as claimed in claim 26,
said width of the midsection being substantially constant between the proximal and distal ends.

30. An undergarment system as claimed in claim 1,
said undergarment comprising a diaper and including an absorbent diaper layer extending along at least part of one of the portions.

\* \* \* \* \*